US012767886B2

(12) United States Patent
Torimoto et al.

(10) Patent No.: US 12,767,886 B2
(45) Date of Patent: Oct. 20, 2026

(54) SEMICONDUCTOR NANO-PARTICLE COMPOSED OF AgAuS-BASED COMPOUND

(71) Applicants: NATIONAL UNIVERSITY CORPORATION TOKAI NATIONAL HIGHER EDUCATION AND RESEARCH SYSTEM, Nagoya (JP); TANAKA KIKINZOKU KOGYO K.K., Tokyo (JP)

(72) Inventors: Tsukasa Torimoto, Nagoya (JP); Tatsuya Kameyama, Nagoya (JP); Shuhei Tsuneizumi, Nagoya (JP); Yumezo Watanabe, Nagoya (JP); Mariko Hasegawa, Nagoya (JP); Hiroki Sato, Tsukuba (JP); Yuusuke Ohshima, Tsukuba (JP)

(73) Assignees: NATIONAL UNIVERSITY CORPORATION TOKAI NATIONAL HIGHER EDUCATION AND RESEARCH SYSTEM, Nagoya (JP); TANAKA PRECIOUS METAL TECHNOLOGIES CO., LTD., Tokyo (JP)

( * ) Notice: Subject to any disclaimer, the term of this patent is extended or adjusted under 35 U.S.C. 154(b) by 551 days.

(21) Appl. No.: 18/278,832

(22) PCT Filed: Feb. 22, 2022

(86) PCT No.: PCT/JP2022/007096
§ 371 (c)(1),
(2) Date: Aug. 24, 2023

(87) PCT Pub. No.: WO2022/181572
PCT Pub. Date: Sep. 1, 2022

(65) Prior Publication Data

US 2024/0150646 A1 May 9, 2024

(30) Foreign Application Priority Data

Feb. 25, 2021 (JP) ................................ 2021-029323

(51) Int. Cl.
*C09K 11/58* (2006.01)
*B82Y 5/00* (2011.01)
(Continued)

(52) U.S. Cl.
CPC .............. *C09K 11/582* (2013.01); *B82Y 5/00* (2013.01); *B82Y 20/00* (2013.01); *C09K 11/025* (2013.01)

(58) Field of Classification Search
CPC ................................ C09K 11/582; C01G 7/00
See application file for complete search history.

(56) References Cited

U.S. PATENT DOCUMENTS 7,326,654 B2 2/2008 Sato et al.
12,441,938 B2 * 10/2025 Torimoto ............ C09K 11/582
(Continued)

FOREIGN PATENT DOCUMENTS

JP 2004-243507 A 9/2004
JP 2004-352594 A 12/2004
(Continued)

OTHER PUBLICATIONS

Li. Reactive AgAuS and Ag3AuS2 Synthons Enable the Sequential Transformation of Spherical Nanocrystals into Asymmetric Multicomponent Hybrid Nanoparticles. Chem. Mater. 2017, 29, 9, 4153-4160 (Year: 2017).*
(Continued)

*Primary Examiner* — Matthew E. Hoban
(74) *Attorney, Agent, or Firm* — Foley & Lardner LLP

(57) ABSTRACT

The present invention is a semiconductor nanoparticle composed of a semiconductor crystal of a compound containing
(Continued)

Ag, Au and S as essential constitutional elements. A AgAuS-based compound constituting the semiconductor nanoparticle has a total content of Ag, Au and S of 95 mass % or more. In addition, the compound is preferably a AgAuS ternary compound represented by the general formula $Ag_{(nx)}Au_{(ny)}S_{(nz)}$. In the formula, n is any positive integer. x, y and z represent proportions of the number of atoms of the respective atoms of Ag, Au and S in the compound and are real numbers satisfying $0<x, y, z\leq 1$, and x/y is 1/7 or more and 7 or less.

6 Claims, 15 Drawing Sheets

(51) Int. Cl.

| | |
|---|---|
| ***B82Y 20/00*** | (2011.01) |
| ***C09K 11/02*** | (2006.01) |

(56) References Cited

U.S. PATENT DOCUMENTS

| | | | | |
|---|---|---|---|---|
| 2005/0145853 | A1 | 7/2005 | Sato et al. | |
| 2008/0187483 | A1 | 8/2008 | Hammami et al. | |
| 2009/0250106 | A1 | 10/2009 | Hayashi et al. | |
| 2018/0066183 | A1 | 3/2018 | Torimoto et al. | |
| 2019/0257784 | A1 | 8/2019 | Jeong et al. | |
| 2023/0247846 | A1* | 8/2023 | Wang | C09K 11/881 252/301.4 R |

FOREIGN PATENT DOCUMENTS

| | | | |
|---|---|---|---|
| JP | 2008-540304 | A | 11/2008 |
| JP | 2017-014476 | A | 1/2017 |
| JP | 2020-502484 | A | 1/2020 |
| TW | 200805402 | A | 1/2008 |

OTHER PUBLICATIONS

Lee. Chemical Reactivity-Controlled Synthesis of Silver Chalcogenide Colloidal Quantum Dots for Efficient Shortwave Infrared Photodetectors. Small 2025, 21, 2412420 (Year: 2025).*

Office Action issued in corresponding Korean Patent Application No. 10-2023-7030881 dated Feb. 7, 2025.

Taiwanese Patent Office, "Office Action," issued in connection with Taiwanese Patent Application No. 111106390, dated Feb. 9, 2023.

International Searching Authority, "International Search Report," issued in connection with International Patent Application No. PCT/JP2022/007096, dated May 10, 2022.

International Searching Authority, "Written Opinion," issued in connection with International Patent Application No. PCT/JP2022/007096, dated May 10, 2022.

Office Action issued in corresponding Japanese Patent Application No. 2023-502414 dated Dec. 2, 2024.

Office Action issued in corresponding Korean Patent Application No. 10-2023-7030881 dated Oct. 25, 2024.

Office Action issued in corresponding Chinese Patent Application No. 202280015993.2 dated Jul. 22, 2025.

European Extended Search Report issued in corresponding European Patent Application No. 22759608.7 dated Dec. 10, 2024.

Office Action issued in corresponding Chinese Patent Application No. 202280015993.2 dated Feb. 12, 2026.

Tang Ling, "Controllable preparation of gold-chalcogenide semiconductor hetero nanorods and their SPR enhancement effect" Chinese Master's Theses Full-text Database: Engineering Science and Technology I, vol. 1, Jan. 15, 2021 (14 pages).

* cited by examiner

SEMICONDUCTOR NANO-PARTICLE COMPOSED OF AgAuS-BASED COMPOUND

CROSS-REFERENCE TO RELATED APPLICATIONS

The present application claims priority under 35 U.S.C. § 371 to International Patent Application No. PCT/JP2022/007096, filed on Feb. 22, 2022, which claims priority to and the benefit of Japanese Patent Application No. 2021-029323, filed on Feb. 25, 2021. The contents of these applications are hereby incorporated by reference in their entireties.

BACKGROUND OF THE INVENTION

Field of the Invention

The present invention relates to a semiconductor nanoparticle composed of a AgAuS-based compound, particularly to a semiconductor nanoparticle having a novel configuration that is a ternary compound composed of Ag, Au and S.

Description of the Related Art

Semiconductors develop a quantum confinement effect when being composed of nano-scale fine particles and have a band gap based on the particle diameters. Therefore, the adjustment of the band gap by controlling the composition and particle diameters of semiconductor nanoparticles makes it possible to arbitrarily set emission wavelengths or absorption wavelengths. Semiconductor nanoparticles for which this characteristic is used are also called quantum dots (QDs) and are expected to be used in a variety of technical fields.

For example, for the semiconductor nanoparticles, studies are underway regarding applications to light-emitting elements and fluorescent substances that are used for display devices, marker substances for detecting bio-related substances and the like. In addition to the fact that the emission wavelengths can be freely controlled by controlling the particle diameters as described above, the semiconductor nanoparticles have an emission peak width that is sufficiently narrow compared with those of organic dyes and are stabler under excitation light irradiation than organic dyes. These facts make it possible to expect application to light-emitting elements and the like.

In addition, the semiconductor nanoparticles are also expected to be used in photoelectric conversion elements or light-receiving elements, which are mounted in solar cells, light sensors and the like. In addition to the absorption wavelengths that can be controlled by the particle diameters, the semiconductor nanoparticles have characteristics of a high quantum efficiency and a high extinction coefficient. These characteristics make it possible for the semiconductor nanoparticles to contribute to the size reduction and thickness reduction of semiconductor devices.

In addition, as specific configurations of the semiconductor nanoparticles, semiconductor nanoparticles composed of a group 12-group 16 compound semiconductor, such as CdS, CdSe or CdTe, a binary compound semiconductor such as a group 14-group 16 compound semiconductor, such as PbS or PbSe, or a ternary compound such as a group 11-group 13-group 16 compound semiconductor, such as AgInTe2, are known (Patent Documents 1 to 3).

Prior Art Document

Patent Documents

Patent Document 1
Japanese Patent Application Laid-Open No. 2004-243507
Patent Document 2
Japanese Patent Application Laid-Open No. 2004-352594
Patent Document 3
Japanese Patent Application Laid-Open No. 2017-014476

SUMMARY OF THE INVENTION

Technical Problem to Be Solved by the Present Invention

Semiconductor nanoparticles that are being applied to a variety of the above-described uses are still in a research stage, and the optimum is not yet found, including the manufacturing methods. Under such circumstances, there are a number of requests for the development of nanoparticles to which a novel compound semiconductor having the above-described peculiar characteristics attributed to the quantum confinement effect and having practical characteristic such as biocompatibility (low-toxic composition) is applied. The present invention has been made based on the above-described circumstances and provides a semiconductor nanoparticle that is composed of a novel compound semiconductor that does not exist in composition examples thus far reported, appropriately has emission and extinction characteristics and also has biocompatibility.

Solution to Problem

The present invention, which solves the above problem, is a semiconductor nanoparticle composed of a semiconductor crystal of a compound containing Ag, Au and S as essential constitutional elements, in which the compound has a total content of Ag, Au and S of 95 mass % or more.

In conventional research examples, there were cases where Ag and Au each served as a constitutional element of a semiconductor nanoparticle separately, but there are no specific study examples regarding the characteristics of a nanoparticle composed of a ternary compound semiconductor containing both Ag and Au. Regarding this fact, according to studies by the present inventors or the like, it has been confirmed that a AgAuS-based compound semiconductor exhibits preferable emission and extinction characteristics when the semiconductor is made into nanoparticles and the composition of Ag and Au is adjusted.

In addition, Ag and Au are both metals that are chemically relatively stable and have been thus far known as biocompatible metals. In addition, S is an essential element of living bodies and is a biocompatible element. Therefore, AgAuS-based compound semiconductor can also be expected to be applied to fluorescent substances and the like that are used in human bodies such as markers or DNA chips.

Hereinafter, a semiconductor nanoparticle composed of a AgAuS-based compound semiconductor of the present invention and a manufacturing method thereof will be described.

A. Configuration of Semiconductor Nanoparticle of Present Invention

As described above, the semiconductor nanoparticle of the present invention is a semiconductor nanoparticle composed of a compound containing Ag, Au and S as essential constitutional elements. This compound composed of Ag, Au and S is specifically a AgAuS ternary compound represented by the general formula $Ag_{(nx)}Au_{(ny)}S_{(nz)}$. At this time, n is any positive integer. x, y and z represent the proportions of the number of atoms of the respective atoms of Ag, Au and S in the compound, and are real numbers satisfying $0<x, y, z\leq 1$. In addition, regarding x and y, which are the proportions of the number of atoms of Ag and Au, x/y is 1/7 or more and 7 or less. z, which is the proportion of the number of atoms of S, is a real number satisfying $0<z\leq 1$ as described above and is preferably a real number satisfying $z\geq(x+y)/2$.

More specific examples of the AgAuS-based compound in the present invention include $Ag_1Au_7S_4$, $AgAu_3S_2$, $Ag_3Au_5S_4$, AgAuS, $Ag_5Au_3S_4$, $Ag_3AuS_2$ and $Ag_7AuS_4$. The AgAuS-based compounds having these specific compositions are compounds having a stoichiometric composition where nx, ny and nz are integers, but the compound that configures the semiconductor nanoparticles of the present invention is not limited to compounds having such a stoichiometric composition.

In addition, regarding x and y, which are the proportions of the number of atoms of Ag and Au, x/y is more preferably 0.3 or more and 3.6 or less. In addition, x and y are more preferably real numbers satisfying that x/(x+y) is 0.33 or more and 0.78 or less. As the AgAuS-based compound having the stoichiometric composition listed above, AgAuS, $Ag_5Au_3S_4$ and $Ag_3AuS_2$ satisfy these conditions. Semiconductor nanoparticles composed of these compounds have a relatively high emission quantum yield and exhibit more effective characteristics as light-emitting elements or the like.

As described above, the semiconductor nanoparticle of the present invention is composed of the AgAuS-based compound represented by $Ag_{(nx)}Au_{(ny)}S_{(nz)}$. This AgAuS-based compound is not limited to be composed of a single phase and may be composed of a mixed phase. For example, the AgAuS-based compound may be a mixed phase of the AgAuS-based compound having the above-described stoichiometric composition ($Ag_3AuS_2$ or the like) and a AgAuS-based compound not having a stoichiometric composition $Ag_{(nx)}Au_{(ny)}S_{(nz)}$: nx, ny and nz are real numbers that are not integers within the above-described range).

The semiconductor nanoparticle of the present invention is composed of a semiconductor crystal of a compound having the above-described configuration in which Ag, Au and S are contained as essential constitutional elements. In this semiconductor crystal, the total content of Ag, Au and S is 95 mass % or more. As elements that can be contained other than Ag, Au and S, which are essential constitutional elements, Ge, Si, Sn, Pb, 0, Se, Te and the like can be considered, but these elements are allowed up to less than 5 mass %. In the compound, the total content of Ag, Au and S is preferably 99 mass % or more and more preferably 99.9 mass % or more. Here, the composition value of the compound is the value of the semiconductor crystal itself in the semiconductor nanoparticle, and the component of a protective agent to be described below is not included.

The semiconductor nanoparticle of the present invention preferably has an average particle diameter of 2 nm or more and 20 nm or less. The particle diameter of the semiconductor nanoparticle correlates with an action of adjusting the band gap by a quantum confinement effect. The average particle diameter is preferably adjusted to be as described above in order to exhibit preferable emission and extinction characteristics by the adjustment of the band gap. The average particle diameter of the semiconductor nanoparticle can be obtained by observing a plurality of (preferably 100 or more) particles with an electron microscope such as TEM, measuring the particle diameter of each particle and calculating the particle number average.

In addition, the semiconductor nanoparticle of the present invention preferably has at least any of an alkylamine having 4 to 20 carbon atoms in an alkyl chain, an alkenylamine having 4 to 20 carbon atoms in an alkenyl chain, an alkylcarboxylic acid having 3 to 20 carbon atoms in an alkyl chain, an alkenylcarboxylic acid having 3 to 20 carbon atoms in an alkenyl chain, an alkanethiol having 4 to 20 carbon atoms in an alkyl chain, a trialkylphosphine having 4 to 20 carbon atoms in an alkyl chain, a trialkylphosphine oxide having 4 to 20 carbon atoms in an alkyl chain, triphenylphosphine and triphenylphosphine oxide as the protective agent bonded to the particle surface. Upon handling the semiconductor nanoparticle, it is common to disperse the semiconductor nanoparticle in an appropriate dispersion medium to produce a solution (also referred to as a slurry or ink in some cases). The protective agent suppresses the agglomeration of the semiconductor nanoparticle in the solution to produce a homogeneous solution or the like and is thus useful. In addition, the protective agent is added to a reaction system together with a raw material in the process for synthesizing the AgAuS compound and thereby acts to form nanoparticles having a suitable average particle diameter. As the protective agent, the above-described alkylamine, alkenylamine, alkylcarboxylic acid, alkenylcarboxylic acid, alkanethiol, trialkylphosphine, trialkylphosphine oxide, triphenylphosphine and triphenylphosphine oxide can be applied singly or in combination.

As thus far described, depending on the particle diameter of the semiconductor nanoparticle, the band gap is adjusted by the quantum confinement effect, and the extinction characteristics change. In the semiconductor nanoparticle of the present invention, the absorption edge wavelength of the absorption spectrum on the long wavelength side is preferably 600 nm or more. This makes the semiconductor nanoparticle have absorbency and responsiveness with respect to light from the visible light range to the near-infrared range.

The semiconductor nanoparticle of the present invention can be applied to a variety of the above-described uses, such as light-emitting elements, by being applied to and supported by appropriate base materials and carriers. The configurations, shapes and dimensions of these base materials and carriers are not particularly limited. As a plate-like, foil-like or film-like base material, for example, glass, quartz, silicon, ceramic, metal and the like are exemplified. In addition, as granular or powdery carriers, inorganic oxides such as ZnO, $TiO_2$, $WO_3$, $SnO_2$, $In_2O_3$ and $Al_2O_3$ are exemplified. In addition, the semiconductor nanoparticle may be supported by the inorganic oxide carrier and, furthermore, fixed to the base material.

In addition, at the time when the semiconductor nanoparticle is applied to and supported by the base material and the carrier, it is common to use a solution, a slurry or an ink containing the semiconductor nanoparticle appropriately dispersed in a dispersion medium as described above. As the dispersion medium such as the solution, chloroform, toluene, cyclohexane, hexane and the like can be applied. In addition, it is possible to apply dipping or a spin coating method as a method for applying the solution or the like of the semiconductor nanoparticle and a variety of methods such as a dropping method, an impregnation method and an adsorption method as a method for supporting.

B. Method for Manufacturing Semiconductor Nanoparticle of Present Invention

The semiconductor nanoparticle to which the AgAuS-based compound semiconductor of the present invention is applied can be manufactured by mixing a Ag precursor, a Au precursor and, if necessary, a S precursor, which is a sulfur source, with a reaction solvent and heating a reaction system composed of these precursors at a temperature of 100° C. or higher and 200° C. or lower. As described above, it is preferable to add at least any of an alkylamine having 4 to 20 carbon atoms in an alkyl chain, an alkenylamine having 4 to 20 carbon atoms in an alkenyl chain, an alkylcarboxylic acid having 3 to 20 carbon atoms in an alkyl chain, an alkenylcarboxylic acid having 3 to 20 carbon atoms in an alkenyl chain, an alkanethiol having 4 to 20 carbon atoms in an alkyl chain, a trialkylphosphine having 4 to 20 carbon atoms in an alkyl chain, a trialkylphosphine oxide having 4 to 20 carbon atoms in an alkyl chain, triphenylphosphine and triphenylphosphine oxide, which is a protective agent, to the reaction system.

As the Ag precursor and the Au precursor, which serve as the raw material, a Ag salt or a Ag complex and a Au salt or a Au complex are each applied. The Ag precursor and the Au precursor are each preferably a salt or complex containing monovalent Ag or monovalent Au. As the Au precursor, a precursor containing trivalent Au can be used. This is because, in the process for synthesizing the semiconductor nanoparticle, trivalent Au is reduced and turned into monovalent Au due to a solvent, a coexisting sulfur compound or the like. In addition, as at least any of the Ag precursor and the Au precursor, it is preferable to apply a complex having a ligand containing a sulfur (S) atom. In this case, the compound can be synthesized using the sulfur atom that is contained in the ligand of the Ag complex and/or the Au complex as the sulfur supply source of the AgAuS-based compound.

Examples of a preferable Ag precursor include silver acetate (Ag(OAc)), silver nitrate, silver carbonate, silver oxide, silver oxalate, silver chloride, silver iodide, silver cyanide salt and the like. In addition, examples of a preferable Au precursor include Au resinate ($C_{10}H_{18}Au_2S_2$: CAS 68990-27-2), chloro(dimethylsulfide)gold (I) ($(CH_3)_2SAuCl$), gold (I) iodide, gold (I) sulfite, chloroauric acid (III), gold (III) acetate, gold (I) cyanide salt, gold (III) cyanide salt, 1,10-phenanthroline gold (III) and the like. In addition, as a sulfur compound that serves as the S precursor, aside from pure sulfur, compounds such as thiourea, alkylthiourea, thioacetamide and alkanethiols and compounds such as β-dithiones, dithiols, xanthates and diethyldithiocarbamate can be applied. Even when the Ag complex or the Au complex is a complex having a ligand containing a S atom, a S compound may be added.

Here, the composition of the AgAuS-based compound to be synthesized (x and y in the general formula $Ag_{(nx)}Au_{(ny)}S_{(nz)}$) can be adjusted by the mixing ratio between the Ag precursor and the Au precursor (charged atomic ratio). In order to obtain a preferable AgAuS-based compound, regarding the amount of the Ag precursor charged and the amount of the Au precursor charged, when the ratio between metal atoms that are contained therein (Ag:Au) is expressed as a:b, a:b is preferably set between 0.78:0.22 to 0.14:0.86 in terms of the atomic ratio. In addition, regarding the amount (c) of S in the reaction system, it is preferable to set the atomic ratio to the total number of the atoms of Ag and Au in the reaction system to 0.25 or more and 4 or less. Regarding the sulfur source, even when excess S is present in the reaction system, the excess S has a small influence on the composition of the AgAuS-based compound.

The reaction system in the synthesis of the semiconductor nanoparticle can be generated in the absence of solvent, or a solvent may be used. In the case of using a solvent, it is possible to apply octadecene, tetradecane, oleic acid, oleylamine, dodecanethiol, a mixture thereof or the like.

The heating temperature (reaction temperature) of the reaction system composed of the Ag precursor, the Au precursor, the S precursor and the protective agent is set to 50° C. or higher and 200° C. or lower. At lower than 50° C., the synthesis of the AgAuS-based compound is difficult to proceed. On the other hand, at higher than 200° C., there is a problem of a concern that Au may singly form a nanoparticle and a compound having a desired composition may not be generated. The average particle diameter of the semiconductor nanoparticle increases with an increase in the reaction temperature, but it is not common for the average particle diameter to exceed the preferable average particle diameter as long as the reaction temperature is within the above-described temperature range. A more preferable reaction temperature is 100° C. or higher and 165° C. or lower. In addition, the heating time (reaction time) can be adjusted by the amount of the raw material charge, but is preferably set to one minute or longer and 60 minutes or shorter. During the synthesis reaction of the semiconductor nanoparticle, it is preferable to stir the reaction system.

After the end of the synthesis reaction of the semiconductor nanoparticle, the reaction system is cooled as necessary, and the semiconductor nanoparticle is collected. At this time, the nanoparticle may be precipitated by adding an alcohol (ethanol, methanol or the like), which serves as a nonsolvent, or the semiconductor nanoparticle may be precipitated by centrifugation or the like, collected, furthermore, the particle may be washed once with an alcohol (ethanol, methanol or the like) or the like and then homogeneously dispersed in a good solvent such as chloroform.

Advantageous Effects of Invention

As described above, the present invention is a semiconductor nanoparticle composed of a AgAuS-based compound. The AgAuS-based compound is a novel composition as a configuration component of the semiconductor nanoparticle and exhibits preferable light characteristics by being made into a nanoparticle. In addition, since a constitutional element thereof is a low-toxic biocompatible element, the semiconductor nanoparticle can also be expected to be applied not only to ordinary semiconductor devices such as light-emitting elements but also to markers and the like that are used in living bodies.

DETAILED DESCRIPTION OF THE PREFERRED EMBODIMENTS

Figure 1:
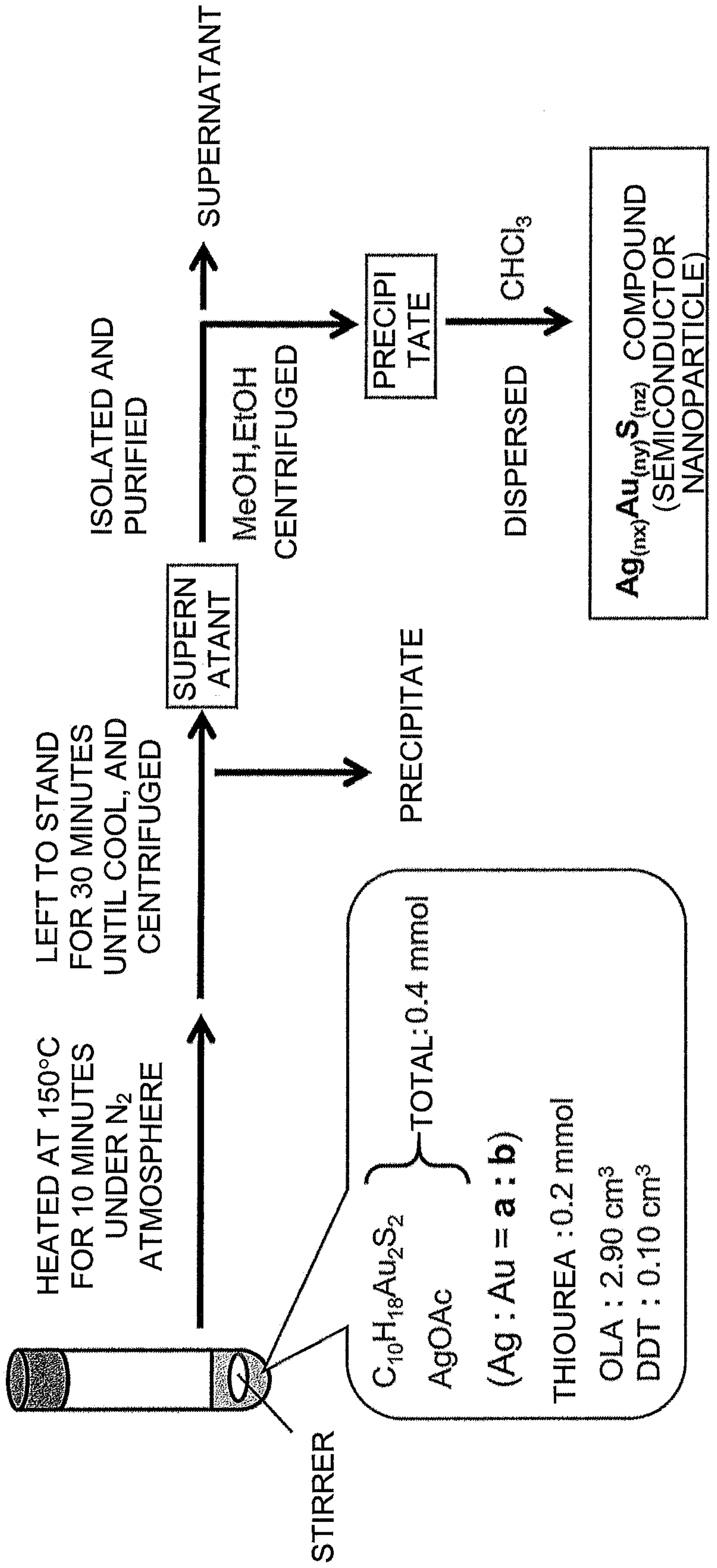
FIG. 1 is a view for describing the outline of steps for manufacturing AgAuS semiconductor nanoparticles of First and Second Embodiments.

First Embodiment: Hereinafter, an embodiment of the present invention will be described. In the present embodiment, semiconductor nanoparticles composed of AgAuS-based compounds ($Ag_{(nx)}Au_{(ny)}S_{(nz)}$) having a variety of compositions were manufactured by adjusting the mixing ratio between a Ag precursor and a Au precursor. In addition, regarding the manufactured semiconductor nanoparticles, the average particle diameters and the crystal structures were confirmed by performing TEM observation and XRD analysis, and then absorption spectra and emission spectra were measured. The outline of the steps for manufacturing the $Ag_{(nx)}Au_{(ny)}S_{(nz)}$semiconductor nanoparticles in the present embodiment is shown in FIG. 1.

As raw materials, silver acetate (Ag(OAc)) as the Ag precursor, Au resinate ($C_{10}H_{18}Au_2S_2$: refer to the following chemical formula) as the Au precursor and 0.2 mmol of thiourea as a S precursor were weighed and put into a test tube, and furthermore, 100 $mm^3$ of 1-dodecanethiol (DDT) as a protecting agent and 2900 $mm^3$ of oleylamine (OLA) as a solvent were added thereto.

[Formula 1]

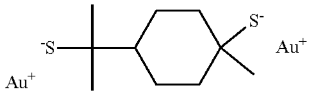

In the present embodiment, the metal atom charged atomic ratio (a:b) of Ag:Au was adjusted while the total amount of silver acetate and Au resinate was maintained at 0.4 mmol. In the present embodiment, seven $Ag_{(nx)}Au_{(ny)}S_{(nz)}$ compounds having charged atomic ratios (a:b) of 1.0:0, 0.78:0.22, 0.60:0.40, 0.45:0.55, 0.33:0.67, 0.14:0.86 and 0:1.0 were synthesized. In addition, each precursor, the protective agent, the solvent and a stirrer were put into the test tube, substituted with nitrogen three times, and then heated and stirred with a hot stirrer for 10 minutes at a reaction temperature set to 150° C. After the end of a reaction, the components were left to stand for 30 minutes until cool and then transferred to a small test tube, centrifugation was performed at 4000 rpm for five minutes, and a supernatant and a precipitate were separated.

Subsequently, 4000 $mm^3$ of methanol was added to the supernatant as a nonsolvent to generate a precipitate, centrifugation was performed at 4000 rpm for five minutes, and the precipitate was collected. Furthermore, this precipitate was dispersed by adding 4000 $mm^3$ of ethanol thereto, then, centrifugation was performed under the same conditions, and a by-product and the solvent were removed to purify the precipitate. The precipitate (semiconductor nanoparticle) thus obtained was dispersed in 4000 $mm^3$ of chloroform, thereby obtaining a dispersion liquid of the semiconductor nanoparticle of the AgAuS-based compound ($Ag_{(nx)}Au_{(ny)}S_{(nz)}$). This dispersion liquid was transferred to a sample bottle, substituted with nitrogen, shielded from light and stored in a refrigerator.

[TEM Observation and Average Particle Diameter Measurement]

Figure 2:
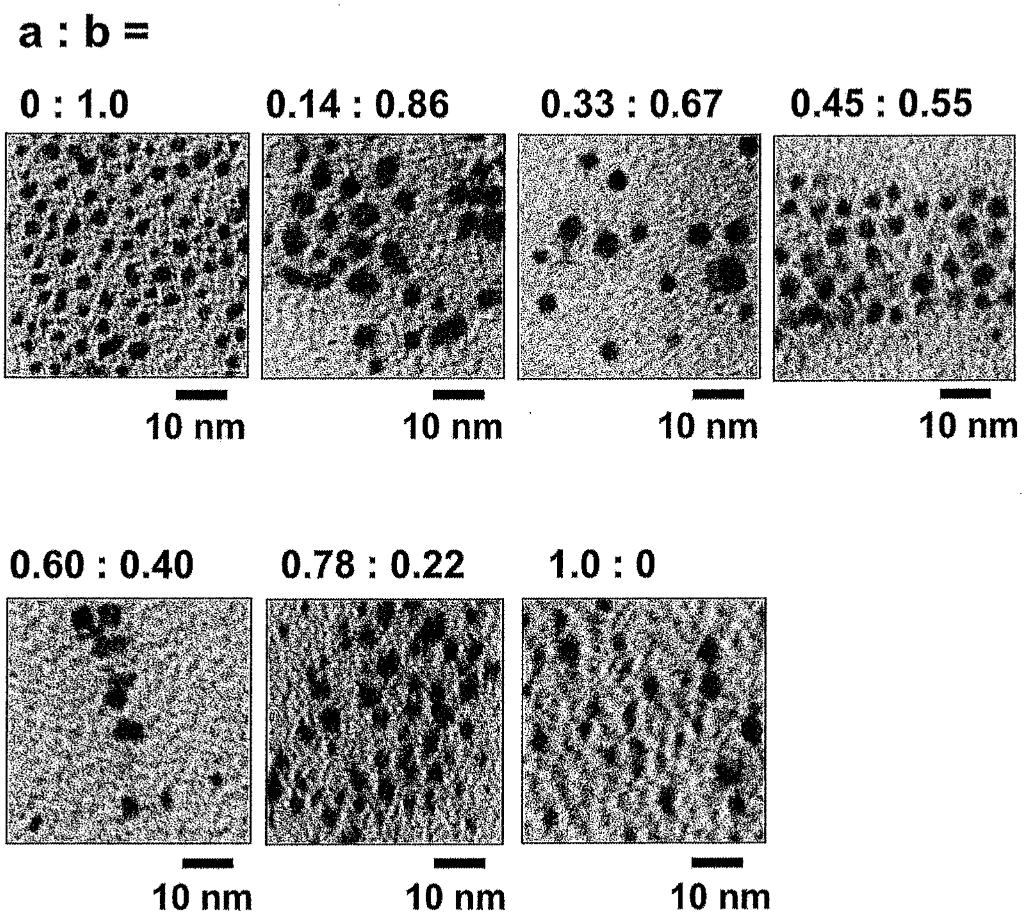
FIG. 2 is TEM images of the AgAuS semiconductor nanoparticles manufactured in First Embodiment.

On the manufactured semiconductor nanoparticles (a:b=1.0:0, 0.78:0.22, 0.60:0.40, 0.45:0.55, 0.33:0.67, 0.14:0.86 and 0:1.0), TEM observation was performed. FIG. 2 shows the TEM images of the semiconductor nanoparticles manufactured in the present embodiment (regarding magnifications, refer to a scale bar (10 nm) on each photograph). From each TEM image, it was confirmed that a substantially spherical semiconductor nanoparticle was synthesized.

Figure 3:
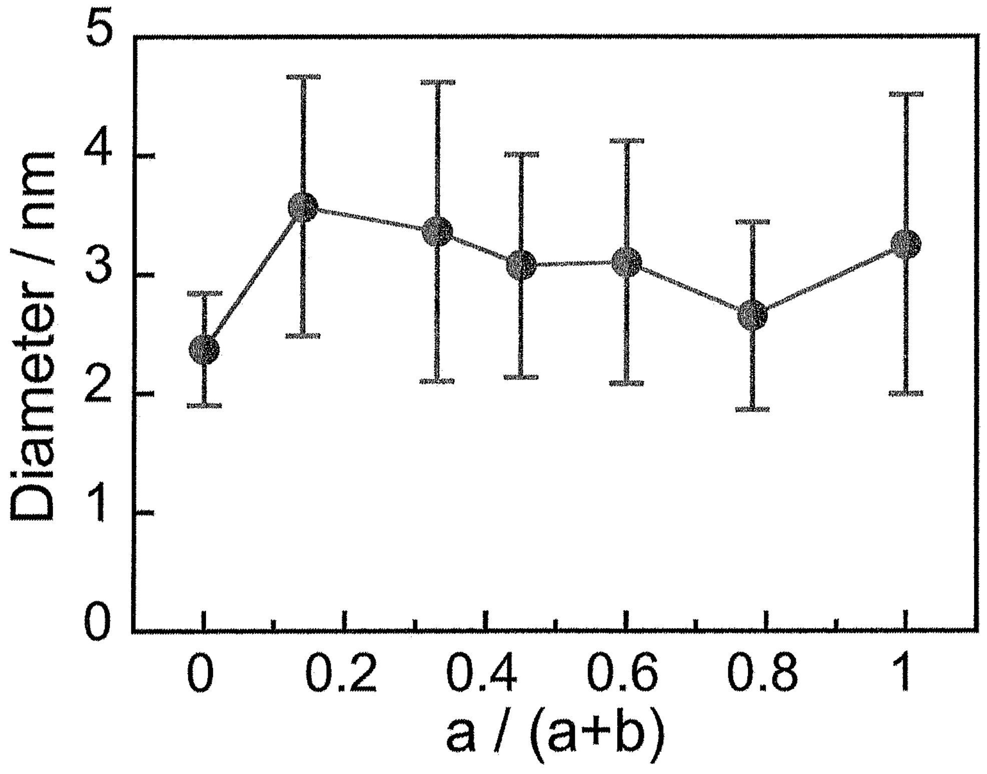
FIG. 3 is a view showing a relationship between the charged atomic ratio a:b of the AgAuS semiconductor nanoparticles manufactured in First Embodiment and the average particle diameter.

Based on the TEM image, the average particle diameter of the semiconductor nanoparticle having each composition was measured and calculated. In the measurement of the particle diameters, particle diameters are obtained from all measurable semiconductor nanoparticles in the TEM image, and the average particle diameter and the standard deviation were calculated. The results are shown in FIG. 3. An error bar for each plot indicates the standard deviation. FIG. 3 shows that the average particle diameters of the semiconductor nanoparticles manufactured in the present embodiment are within a range of 2 nm to 5 nm. Regarding the proportions of Ag and Au, the particle with a:b=0:1 ($Au_2S$) is liable to have small particle diameters, but there is no significant difference in other particles.

[Composition Analysis of Semiconductor Nanoparticle]

ICP analysis was performed together with the above-described TEM observation, thereby analyzing the compositions of semiconductor nanoparticle samples. The ICP analysis was performed using Agilent 5110 manufactured by Agilent Technologies International Japan, Ltd. as a measuring instrument by performing a pretreatment by a microwave acid digestion method and then performing measurement at a RF power of 1.2 kW, a plasma gas flow rate of 12 L/min. and an auxiliary gas flow rate of 1.0 L/min. The analysis results for the seven semiconductor nanoparticles for which the charged atomic ratios (a:b) between Ag and Au were set to 1.0:0, 0.78:0.22, 0.60:0.40, 0.45:0.55, 0.33:0.67, 0.14:0.86 and 0:1.0 are shown in Table 1. It was found from Table 1 that the atomic ratios (x:y:z) of the semiconductor nanoparticles manufactured in the present embodiment do not completely coincide with the charged atomic ratio (a:b) between the metal precursors but are close values. The cation/anion ratios ((x+y)/(2z)) showed values of 0.78 to 0.95, and the semiconductor particles were composed of a non-stoichiometric composition in which a cation was deficient. For the semiconductor nanoparticles synthesized in the present embodiment, the total concentration of Ag, Au and S in a AgAuS compound were 100 mass %.

TABLE 1

| Charged atomic ratio (a:b) | Compound composition (atomic ratio) Ag x | Au y | S z | (x + y)/(2z) |
|---|---|---|---|---|
| 1.0:0 | 1.0 | 0 | 0.64 | 0.78 |
| 0.78:0.22 | 0.78 | 0.22 | 0.61 | 0.82 |
| 0.60:0.40 | 0.68 | 0.32 | 0.60 | 0.83 |
| 0.45:0.55 | 0.54 | 0.46 | 0.63 | 0.79 |
| 0.33:0.67 | 0.46 | 0.54 | 0.61 | 0.82 |
| 0.14:0.86 | 0.27 | 0.73 | 0.53 | 0.95 |
| 0:1.0 | 0 | 1.0 | 0.61 | 0.82 |

[XRD Analysis]

Figure 4:
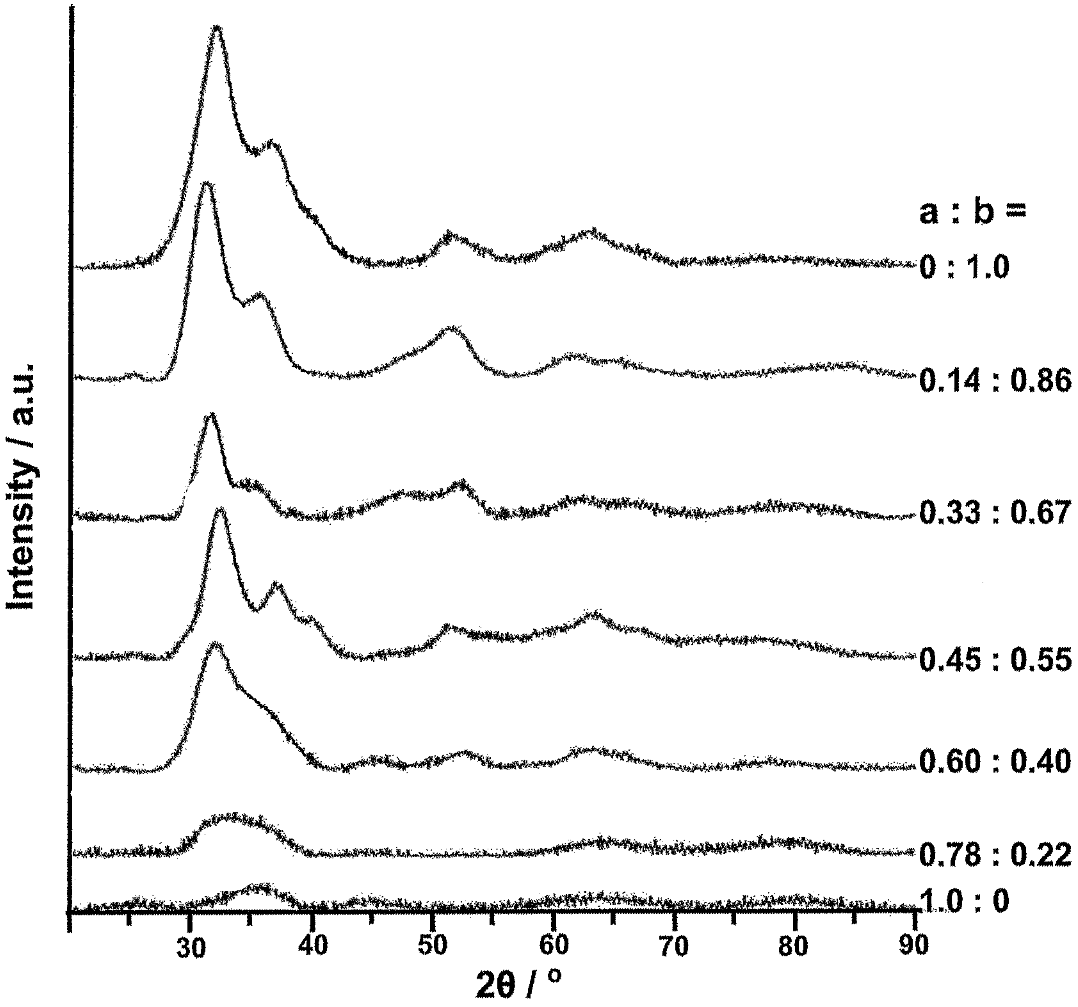
FIG. 4 is a view showing XRD diffraction patterns of the AgAuS semiconductor nanoparticles manufactured in First Embodiment.
Figure 5A:
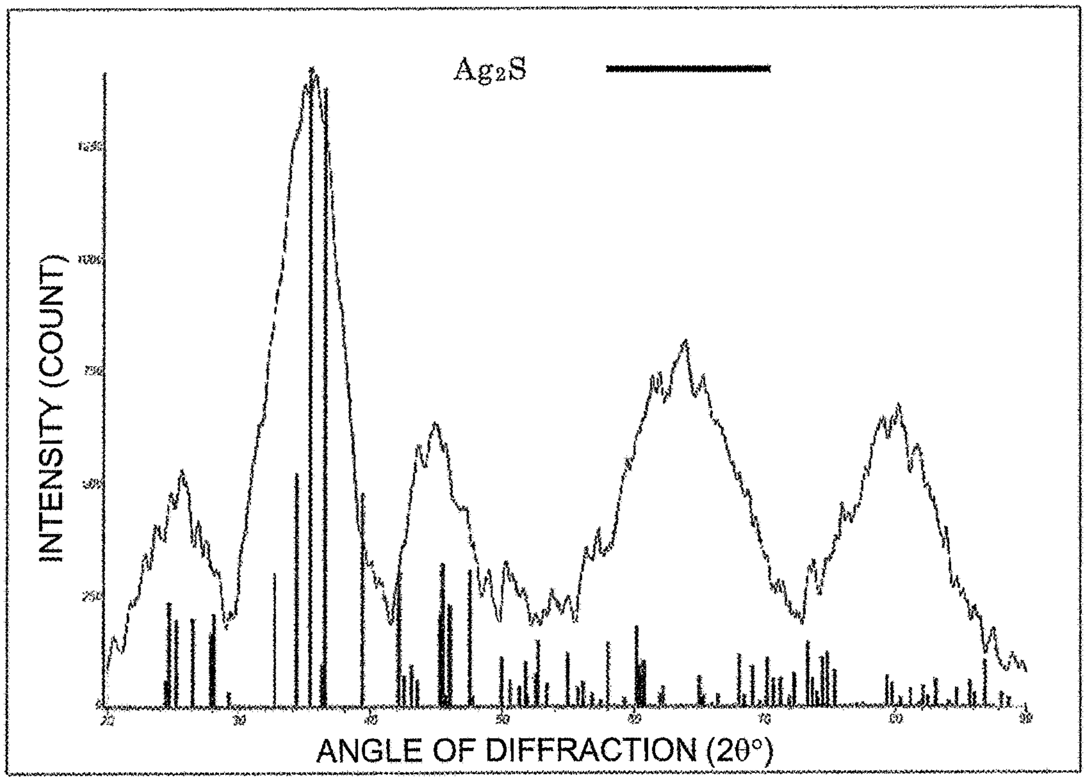
FIG. 5*a* is a view showing an XRD diffraction pattern of the AgAuS semiconductor nanoparticle (charged atomic ratio a:b=1:0) manufactured in First Embodiment.
Figure 5B:
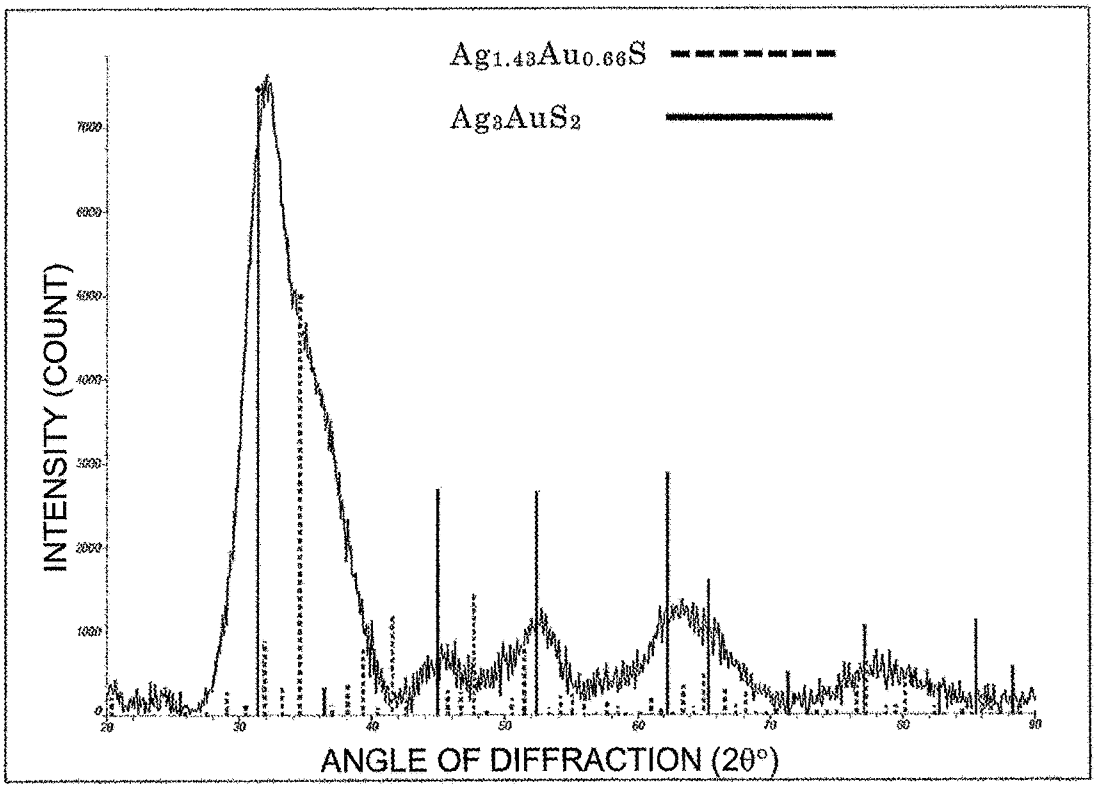
FIG. 5*b* is a view showing XRD diffraction patterns of the AgAuS semiconductor nanoparticles (charged atomic ratio a:b=0.60:0.40) manufactured in First Embodiment.
Figure 5C:
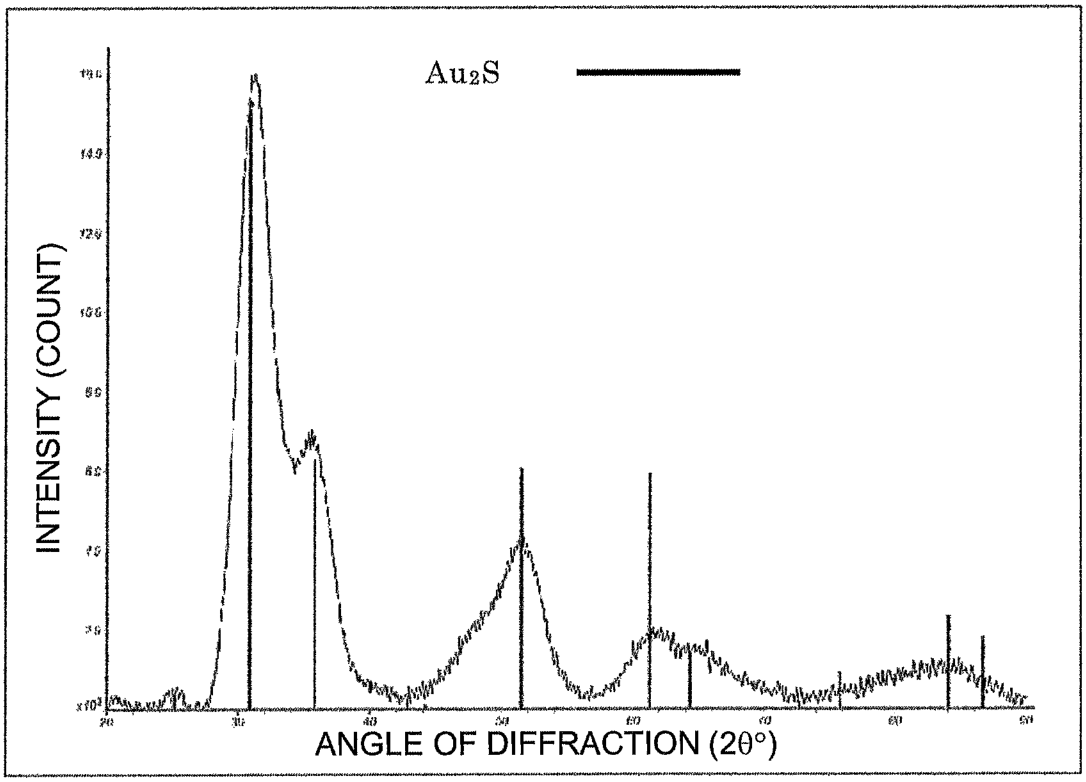
FIG. 5*c* is a view showing an XRD diffraction pattern of the AgAuS semiconductor nanoparticle (charged atomic ratio a:b=0:1) manufactured in First Embodiment.

XRD analysis was performed on each semiconductor nanoparticle. An XRD analyzer was Ultima IV manufactured by Rigaku Corporation, CuKa 10 rays were used as characteristic X rays, and 1°/m in. was set as an analysis condition. FIG. 4 shows the diffraction patterns of the seven nanoparticles manufactured in the present embodiment. Furthermore, among them, the diffraction patterns of the three nanoparticles for which the charged atomic ratios (a:b) between Ag and Au were 0:1.0, 0.60:0.40 and 0:1.0 are enlarged 15 and shown in FIG. 5*a* to FIG. 5*c*. FIG. 5*c* shows that, from the nanoparticle for which the charged atomic ratio was 0:1.0, a peak coinciding with the diffraction peak of $Au_2S$ is obtained. In addition, FIG. 5*a* shows that, from the semiconductor nanoparticle for which the charged atomic ratio was 1.0:0, while there is a mismatch in a part of the peak on the high angle side, a peak near 35° C. to 37° C. that is derived from the diffraction of $Ag_2$ S is observed. On the other hand, when FIG. 5*b* is referred to, from the semiconductor nanoparticle for which the charged atomic ratio was 0.60:0.40, not only a peak derived from Ag3AuS2 but also a peak derived from Ag1.43Au0.66S were observed. From these facts, it is considered that, for these semiconductor nanoparticles, Table 1 shows that all of the compounds had compositions of $Ag_{n(0.68)}AU_{n(0.32)}S_{n(0.6)}$ (x=0.68, y=0.32, z=0.60) but were possibly composed of a mixed phase of $Ag_3AuS_2$ and $Ag_{1.43}Au_{0.66}S$.

In addition, when FIG. 4 is referred to, it is confirmed that, in the semiconductor nanoparticles for which the charged metal ratios (Ag:Au) were 0.78:0.22, 0.60:0.40, 0.45:0.55, 0.33:0.67 and 0.14:0.86, as the ratio of Ag increases and the ratio of Au decreases, the peak patterns gradually changed from $Au_2S$ to $Ag_2S$. The XRD analysis of the present embodiment does not make it possible to determine the structure and composition of a solid solution of the particle synthesized with each charged atomic ratio or to determine the composition and abundance of a mixture in a case where the mixture coexist, but makes it possible to confirm that crystalline particles could be synthesized in all of the charged compositions.

[Measurement of Absorption Spectrum and Emission Spectrum]

Figure 6:
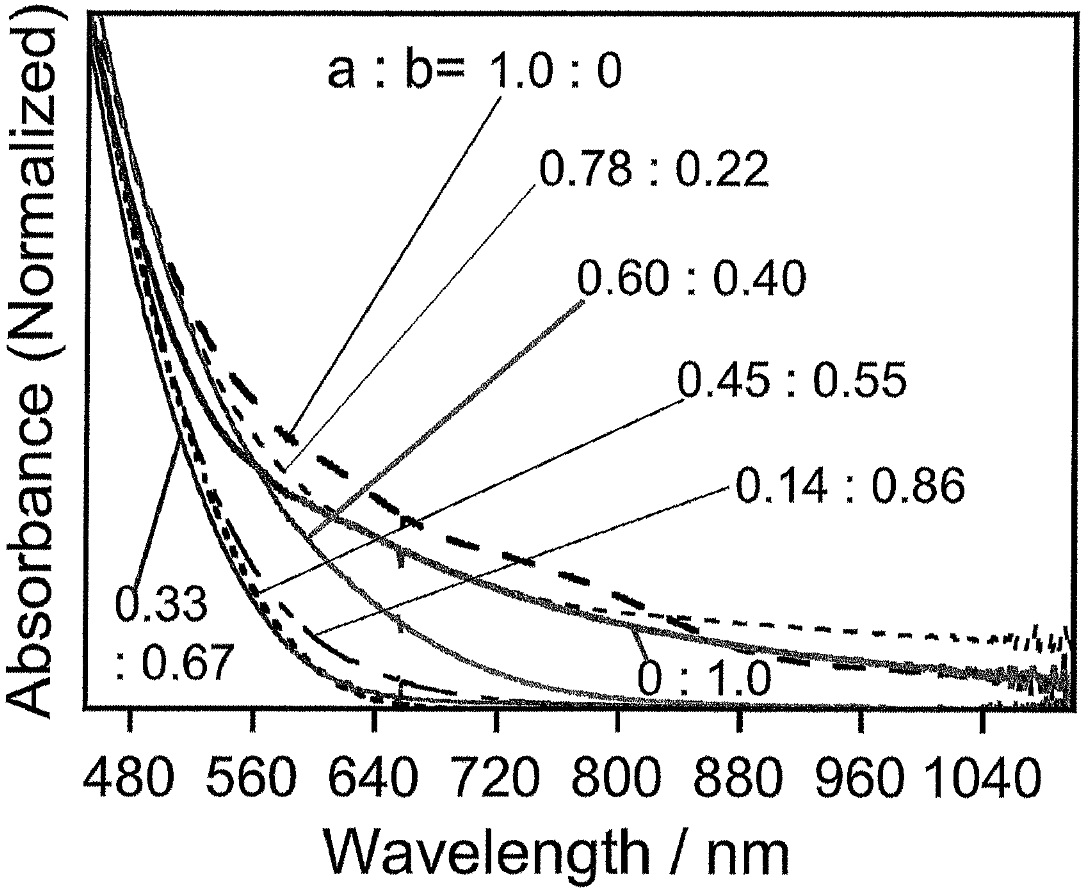
FIG. 6 is a view showing the measurement results of the absorption spectra of the AgAuS semiconductor nanoparticles manufactured in First Embodiment.

Next, for each semiconductor nanoparticle, the absorption spectrum and the emission spectrum were measured. The absorption spectrum was measured using a UV-Visible spectrophotometer (manufactured by Agilent Technologies International Japan, Ltd., Agilent 8453) within a wavelength range of 400 nm to 1100 nm. The measurement results of the absorption spectra of the semiconductor nanoparticles of the present embodiment are shown in FIG. 6.

The emission spectrum was measured using a fluorescence spectrophotometer (manufactured by Hamamatsu Photonics K.K., PMA-12) at an excitation wavelength set to 365 nm. At this time, the sample was adjusted in a chloroform solution (n=1.4429) so that the absorbance at 365 nm reached 0.1, and the measurement was performed.

In addition, for the measurement of the emission quantum yield, an absolute PL quantum yield spectrometer (manufactured by Hamamatsu Photonics K.K., C9920-03) was used. In a case where emission was observed at a long wavelength of 1000 nm or longer, the emission spectrum was measured using a photonic multichannel analyzer (manufactured by Hamamatsu Photonics K.K., PMA-12 (model Nos.: C10027-02 (wavelength range: 350 to 1100 nm) and 10028-01 (wavelength range: 900 to 1650 nm)). At this time, the sample was adjusted in a chloroform solution (n=1.4429) so that the absorbance at 700 nm reached 0.1, and the measurement was performed. The excitation light wavelength was set to 700 nm in the measurement. For the calculation of the emission quantum yield, regarding the emission spectrum measured with the fluorescence spectrophotometer, the emission spectrum of an ethanol solution (n=1.3618) of indocyanine green (ICG: Φ=13.2%), which is a near-infrared emitting organic fluorescent dye, was measured as a standard specimen, and the emission quantum yield of each sample was calculated from the following expression by the comparative method.

$$\Phi_x = \Phi_{st} \times \left(\frac{FA_x}{FA_{st}}\right) \times \left(\frac{A_{st}}{A_x}\right) \times \left(\frac{I_{ex}, st}{I_{ex}, x}\right) \times \left(\frac{n_x^2}{n_{st}^2}\right) \quad \text{[Expression 1]}$$

(A: Absorbance of specimen at excitation wavelength,
lex: Intensity of excitation light at excitation wavelength,
n: Refractive index of solvent)

Figure 7:
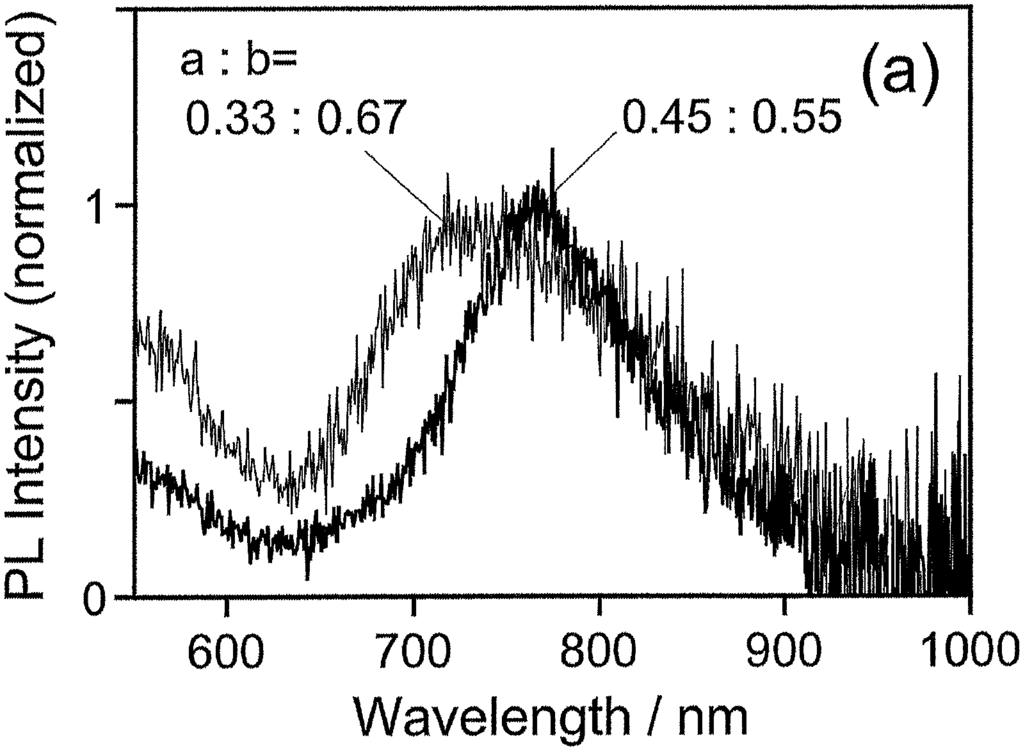
FIG. 7 is a view showing the measurement results of the emission spectra of the AgAuS semiconductor nanoparticles manufactured in First Embodiment.
Figure 7:
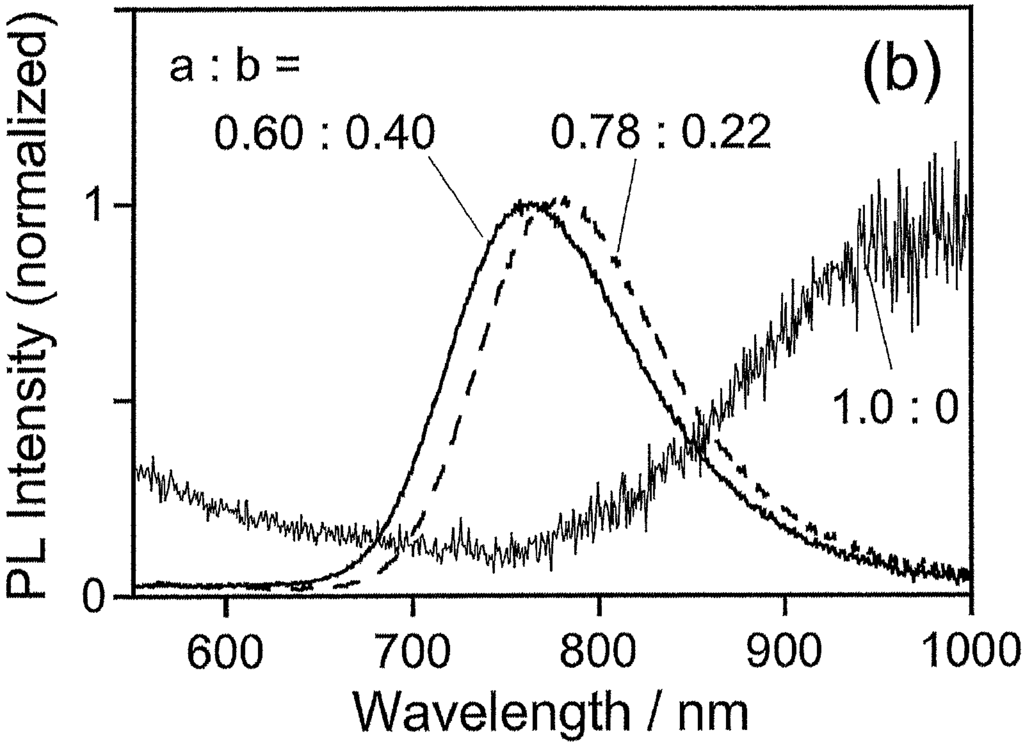
Figure 8:
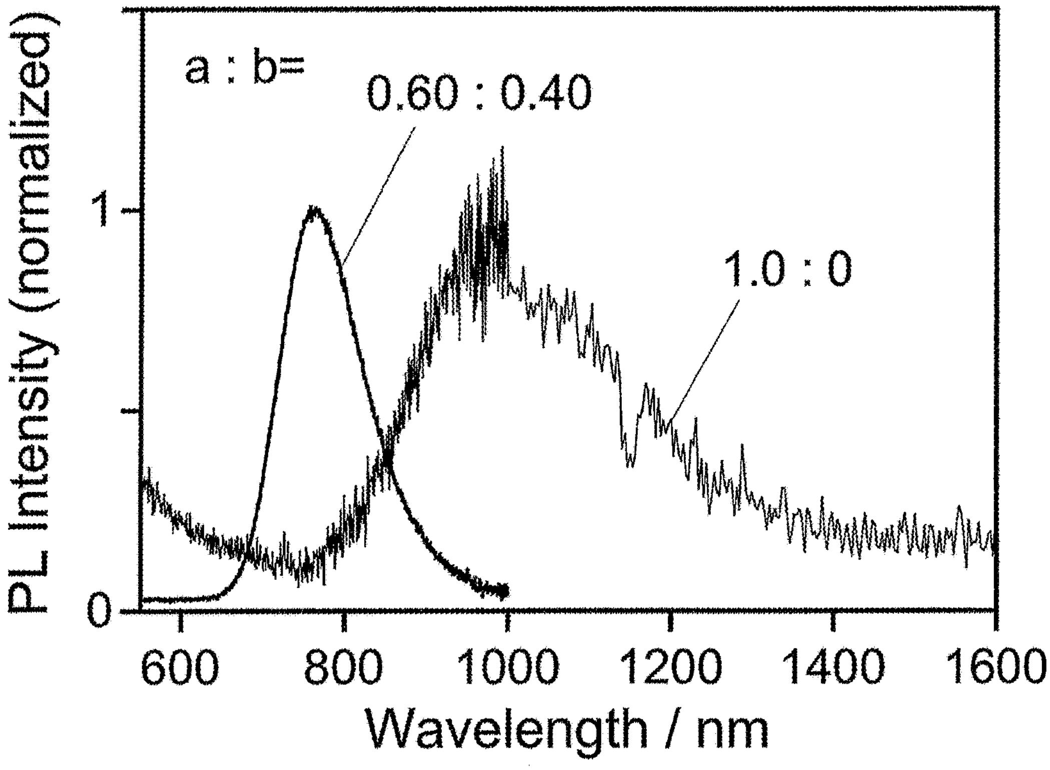
FIG. 8 is a view showing the measurement results of the emission spectra of the AgAuS semiconductor nanoparticles (long wavelength region) manufactured in First Embodiment.
Figure 9:
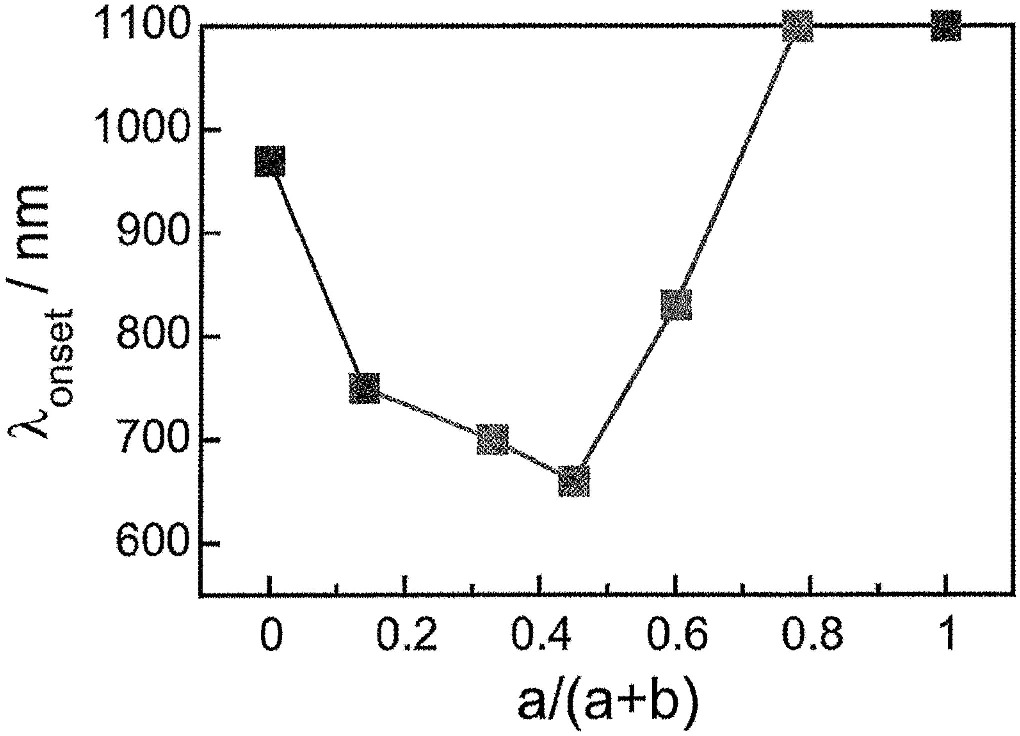
FIG. 9 is a view showing a relationship between the charged atomic ratio a:b of the AgAuS semiconductor nanoparticles manufactured in First Embodiment and the absorption edge wavelength.

The emission spectra of the semiconductor nanoparticles of the present embodiment measured and calculated as described above are shown in FIG. 7 and FIG. 8. In addition, the relationship between the charged atomic ratio a:b of the semiconductor nanoparticle obtained from FIG. 6 and the long wavelength-side absorption edge wavelength is shown in FIG. 9. In addition, the relationship between the charged atomic ratios a:b of the semiconductor nanoparticles of the present embodiment, which are obtained from FIG. 7 and FIG. 8, and the emission quantum yields is shown in FIG. 10.

FIG. 9 shows that, in the semiconductor nanoparticles for which a:b=1.0:0 ($Ag_2S$) and 0.78:0.22, the absorption edge wavelengths reached up to a long wavelength range of 1100 nm or longer and accurate measurement was not possible. The absorption edge wavelength once shifted toward the short wavelength side from a:b=0.78:0.22 as the Ag proportion decreased and became the shortest wavelength (660 nm) when a:b was 0.45:0.55. When the Ag proportion further decreased from the above, the absorption edge wavelength shifted toward the long wavelength side again and was expected to reach 970 nm in the particle for which a:b=0:1.0 ($Au_2S$). In the semiconductor nanoparticle composed of $Ag_{(nx)}Au_{(ny)}S_{(nz)}$ of the present invention, it was confirmed that the absorption edge wavelength is 600 nm or longer.

Figure 10:
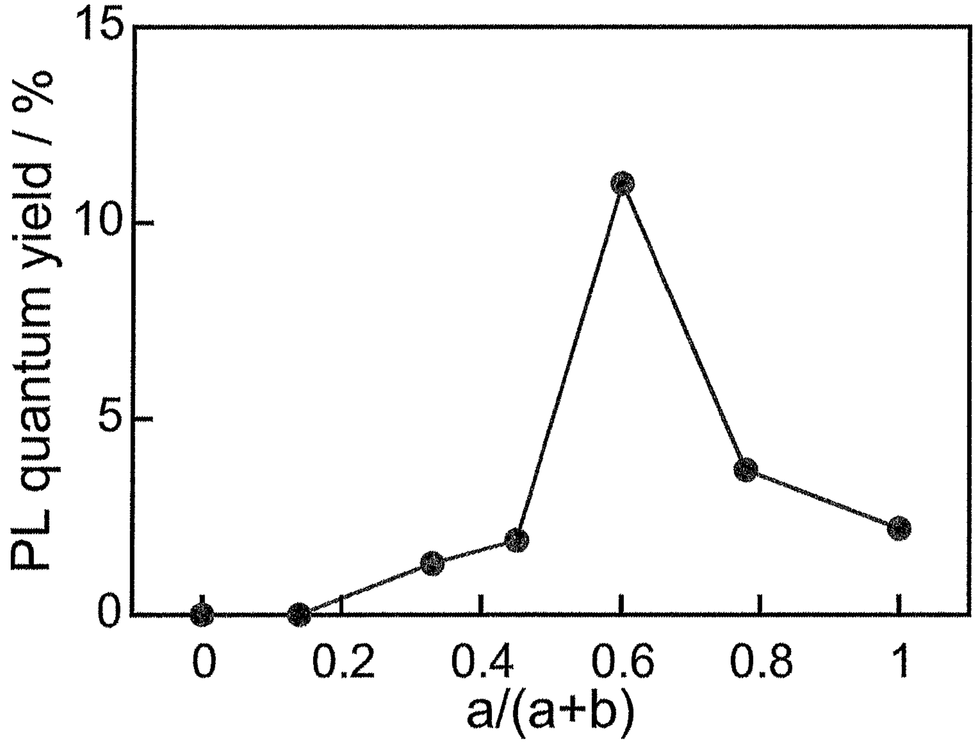
FIG. 10 is a view showing a relationship between the charged atomic ratio a:b of the AgAuS semiconductor nanoparticles manufactured in First Embodiment and the emission quantum yield.

In addition, it is found from FIG. 10 that the emission quantum yield of the semiconductor nanoparticle of the present embodiment is maximized at a charged atomic ratio (a:b) of near 0.60:0.40. In the semiconductor nanoparticle composed of $Ag_{(nx)}Au_{(ny)}S_{(nz)}$ of the present invention, when a:b=1.0:0 or 0:1.0 is considered as a reference example ($Ag_2S$ or $Au_2S$), it is considered that the semiconductor nanoparticles synthesized at a:b=0.33:0.67 to 0.78:0.22 are particularly preferable. In addition, Table 1 shows that, in the semiconductor nanoparticles manufactured at the preferable charged atomic ratios, the atom proportions of Ag and Au (x, y) are 0.46 to 0.78 in terms of x/(x+y), that is, x/y is 0.85 to 3.5.

Second Embodiment: In the present embodiment, semiconductor nanoparticles composed of a $Ag_{(nx)}Au_{(ny)}S_{(nz)}$ compound were manufactured using silver acetate and gold resinate by changing the reaction temperature during synthesis while the charged atomic ratio (a:b) between the metal atoms is fixed to 0.60:0.40, the average particle diameters were measured, and the absorption spectra and the emission spectra were measured. The steps for manufacturing the $Ag_{(nx)}Au_{(ny)}S_{(nz)}$ semiconductor nanoparticles are basically the same as those in First Embodiment. In FIG. 1, the total amount of silver acetate and Au resinate was set to 0.4 mmol, and each metal charged atomic ratio a:b was set to 0.60:0.40, thereby forming a reaction system. In addition, the semiconductor nanoparticles were manufactured under five conditions where the reaction temperature was 100° C., 125° C., 150° C., 165° C. or 175° C.

[TEM Observation and Average Particle Diameter Measurement]

Figure 11:
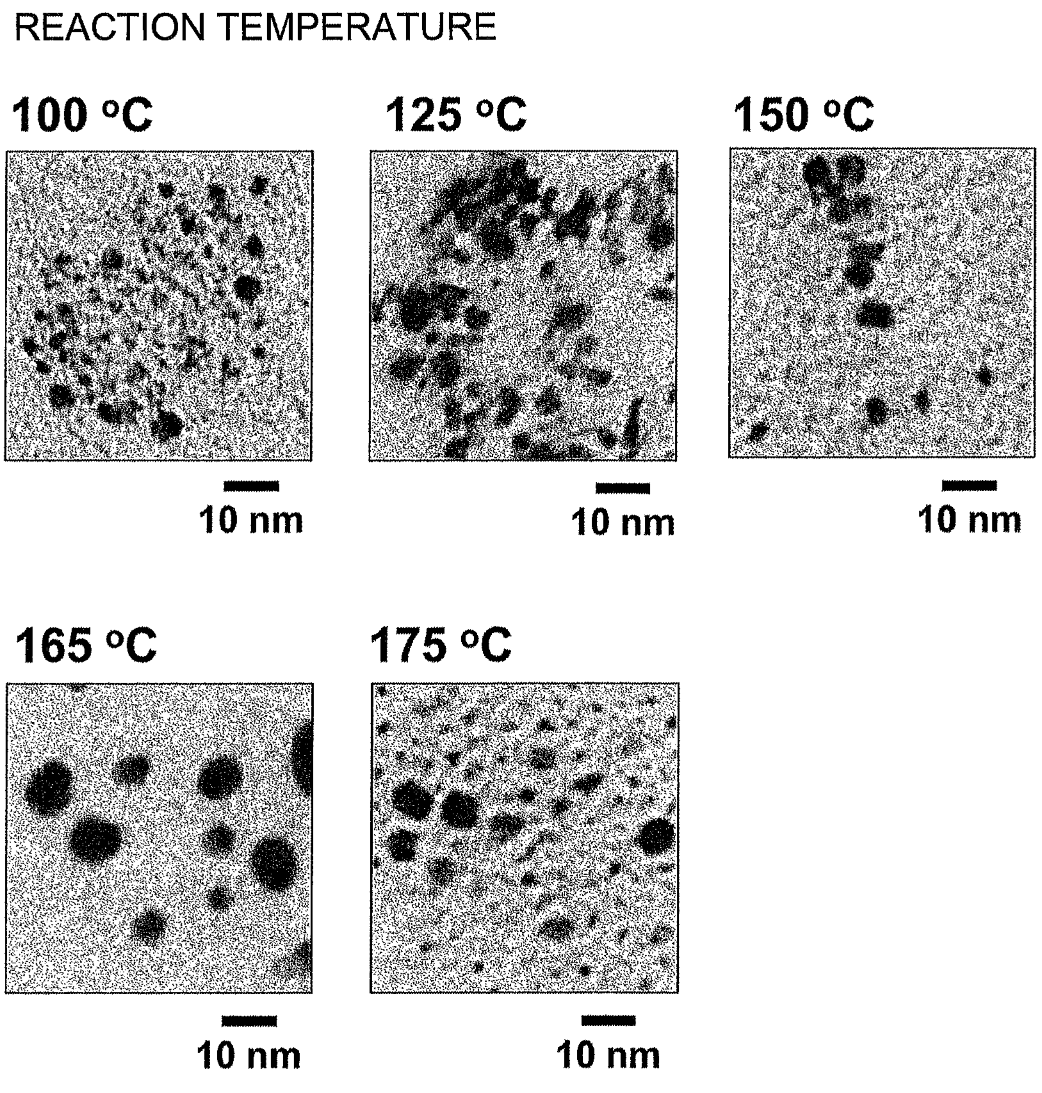
FIG. 11 is TEM images of the AgAuS semiconductor nanoparticles manufactured in Second Embodiment.
Figure 12:
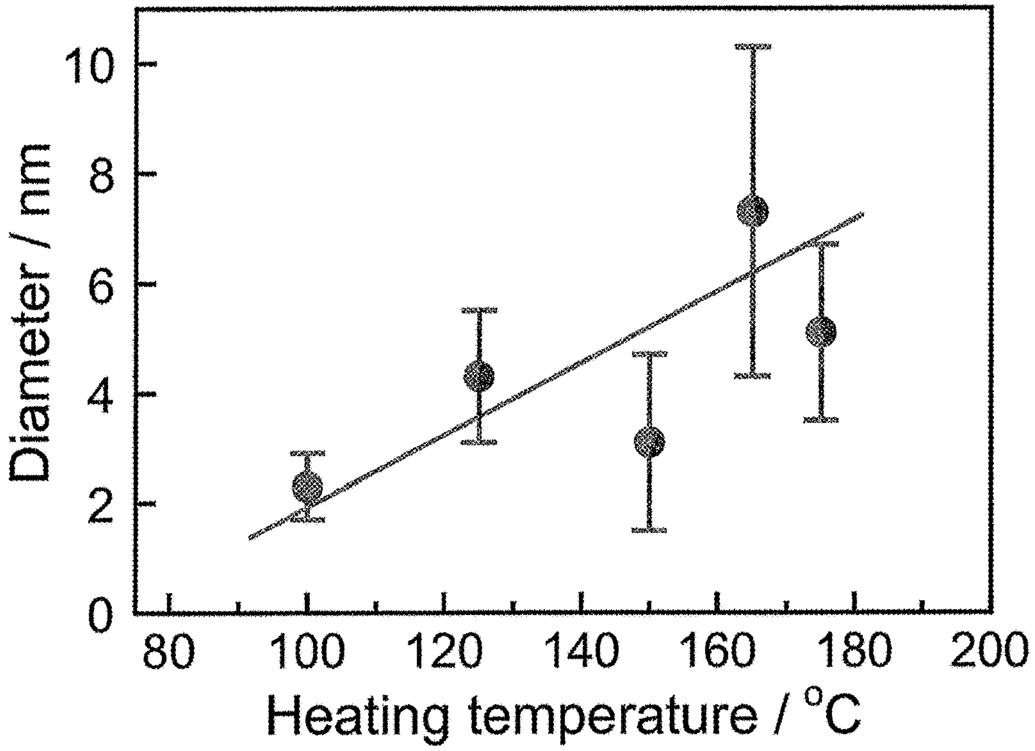
FIG. 12 is a view showing a relationship between the reaction temperature of the AgAuS semiconductor nanoparticles manufactured in Second Embodiment and the average particle diameter.

On the semiconductor nanoparticle manufactured at each reaction temperature, TEM observation was performed in the same manner as in First Embodiment. FIG. 11 shows a TEM image of each semiconductor nanoparticle. From FIG. 11, the generation of substantially spherical nanoparticles is confirmed even in the present embodiment. In addition, FIG. 12 shows the relationship between the reaction temperature and the average particle diameter measured regarding each semiconductor nanoparticle. The fact that the particle diameter of the semiconductor nanoparticle increases as the reaction temperature increases is revealed. This is considered to be attributed to the fact that an increase in the reaction temperature promotes crystal growth.

[Measurement of Absorption Spectrum and Emission Spectrum]

For each semiconductor nanoparticle, the absorption spectrum and the emission spectrum were measured. Methods for measuring these were the same as those in First Embodiment.

Figure 13:
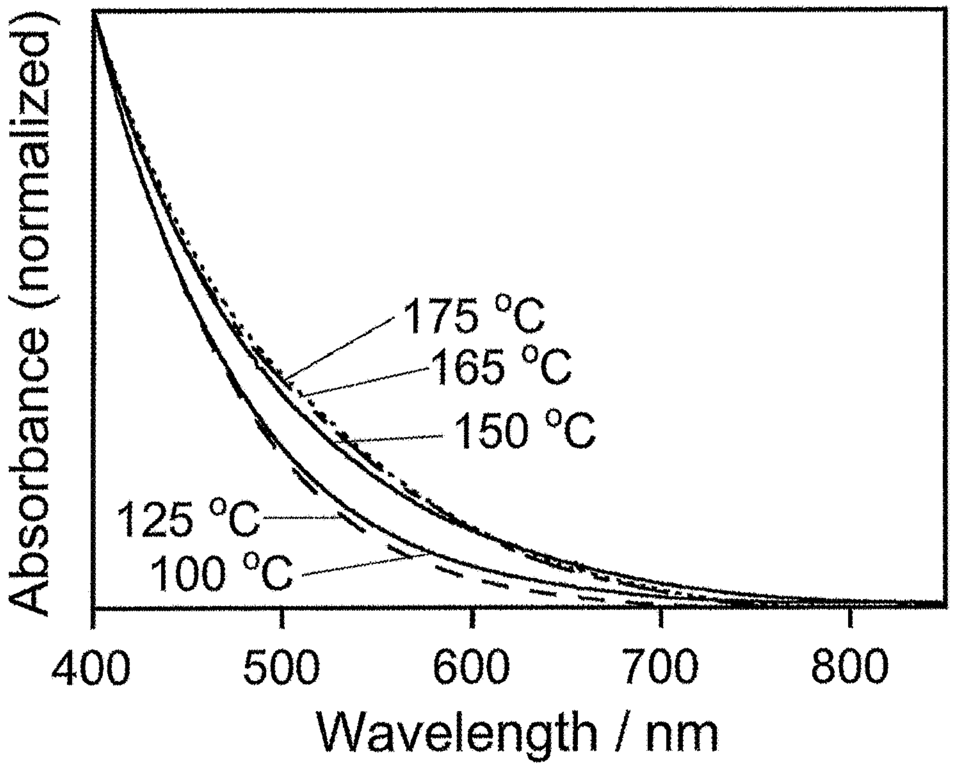
FIG. 13 is a view showing the measurement results of the absorption spectra of the AgAuS semiconductor nanoparticles manufactured in Second Embodiment.
Figure 14:
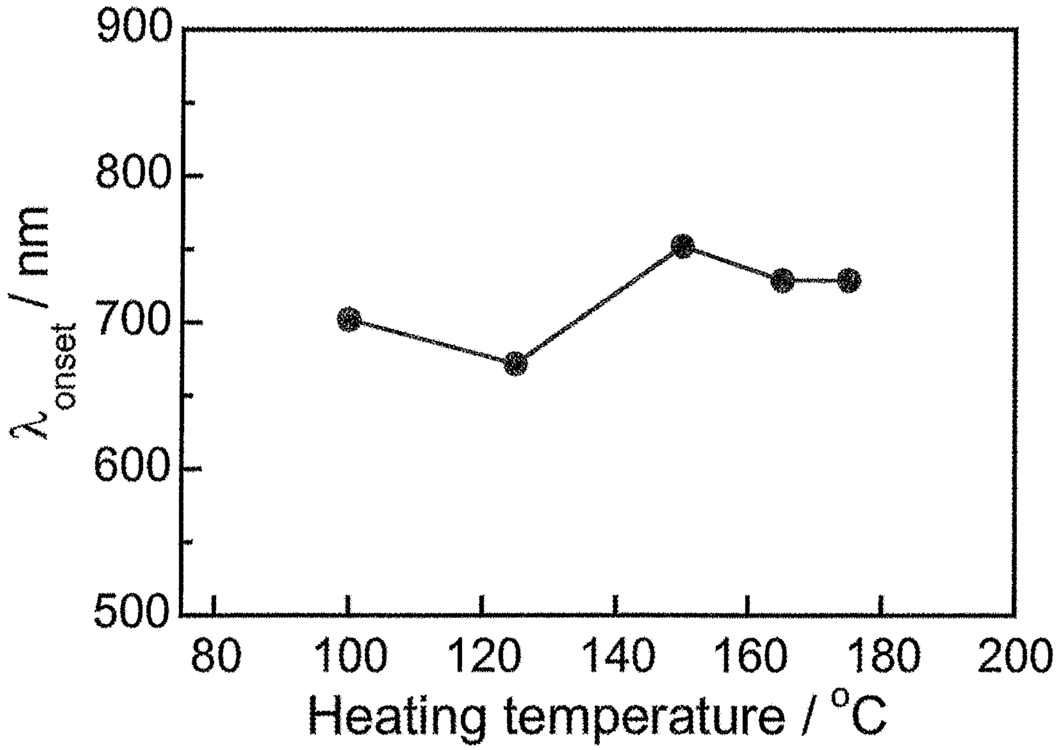
FIG. 14 is a view showing a relationship between the reaction temperature of the AgAuS semiconductor nanoparticles manufactured in Second Embodiment and the absorption edge wavelength.

The measurement results of the absorption spectra of the semiconductor nanoparticles of the present embodiment are shown in FIG. 13. In addition, the relationship between the reaction temperature and the long wavelength-side absorption edge wavelength obtained from the measurement results of the absorption spectra is shown in FIG. 14. FIG. 14 shows that, even when the reaction temperatures changed, the absorption edge wavelengths of the semiconductor nanoparticles were not significantly affected and were almost constant at 650 to 750 nm. Even for the semiconductor nanoparticles manufactured in the present embodiment, it was confirmed that the absorption edge wavelengths were 600 nm or longer.

Figure 15:
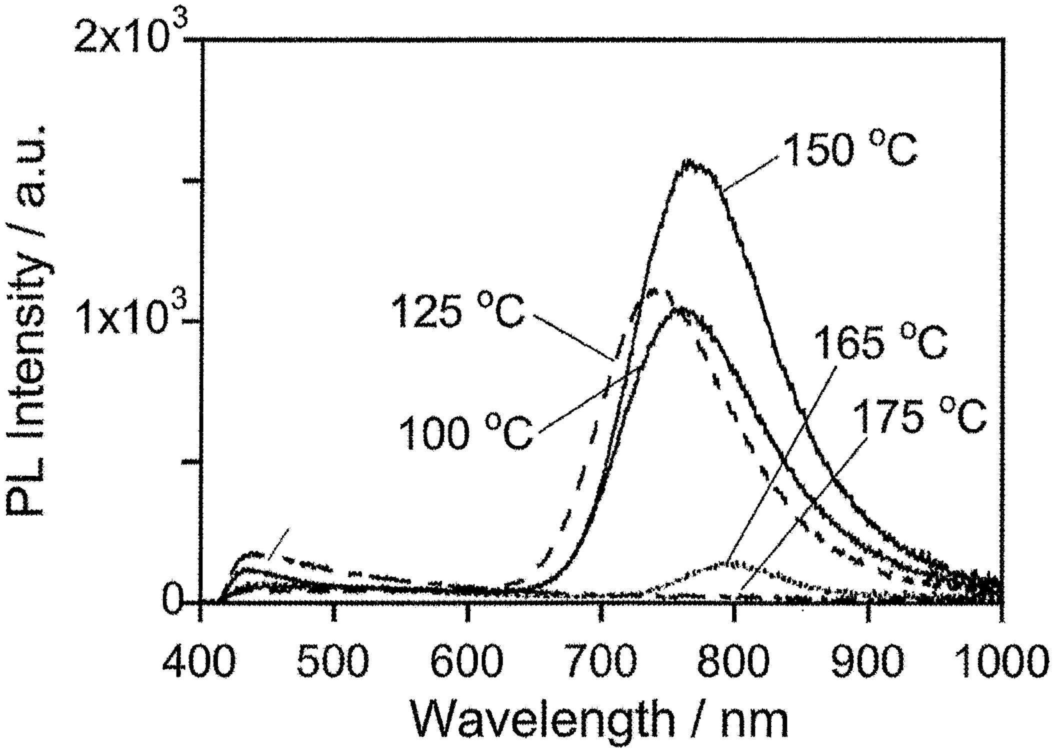
FIG. 15 is a view showing the measurement results of the emission spectra of the AgAuS semiconductor nanoparticles manufactured in Second Embodiment.
Figure 16:
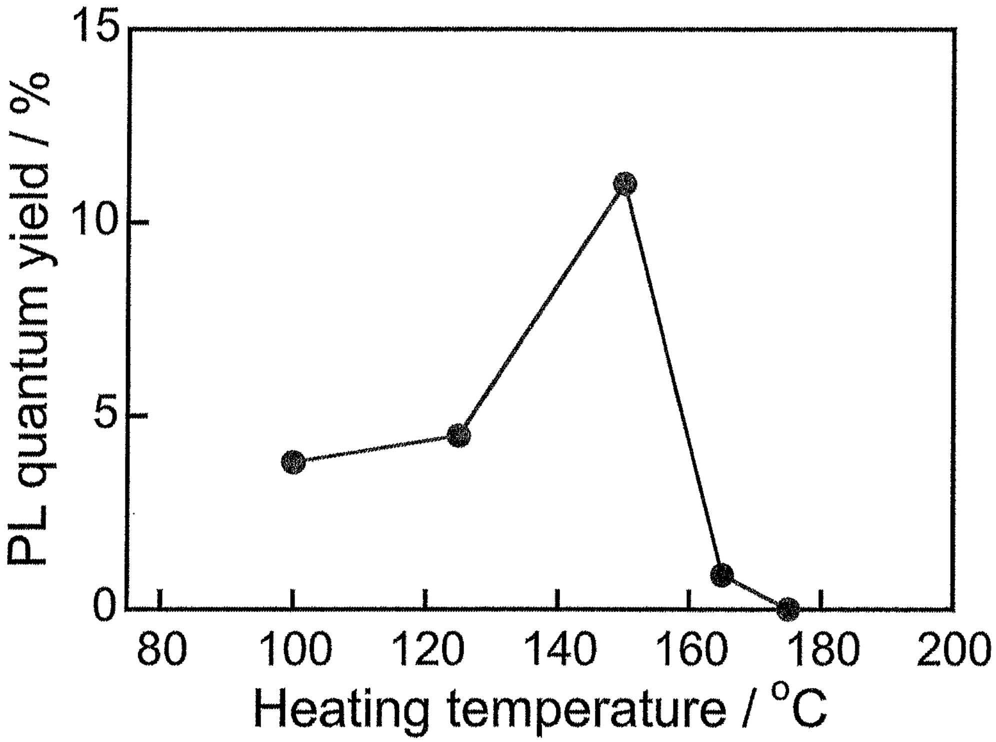
FIG. 16 is a view showing a relationship between the reaction temperature of the AgAuS semiconductor nanoparticles manufactured in Second Embodiment and the emission quantum yield.

In addition, the emission spectra of the semiconductor nanoparticles of the present embodiment are shown in FIG. 15. It is found from FIG. 15 that, at the reaction temperatures of 100° C. to 165° C., the emission peak wavelengths of the semiconductor nanoparticles are 700 to 800 nm and almost do not change. At 175° C., no emission peak was detected. The relationship between the reaction temperatures of the semiconductor nanoparticles manufactured in the present embodiment and the emission quantum yields is shown in FIG. 16. FIG. 16 shows that, within a range of 100° C. to 150° C., the emission quantum yield of the obtained semiconductor nanoparticle increased as the reaction temperature increased. On the other hand, when the reaction temperatures were further increased to 165° C. and 175° C., the emission quantum yields of the obtained semiconductor nanoparticles conversely decreased.

[XRD Analysis]

Figure 17:
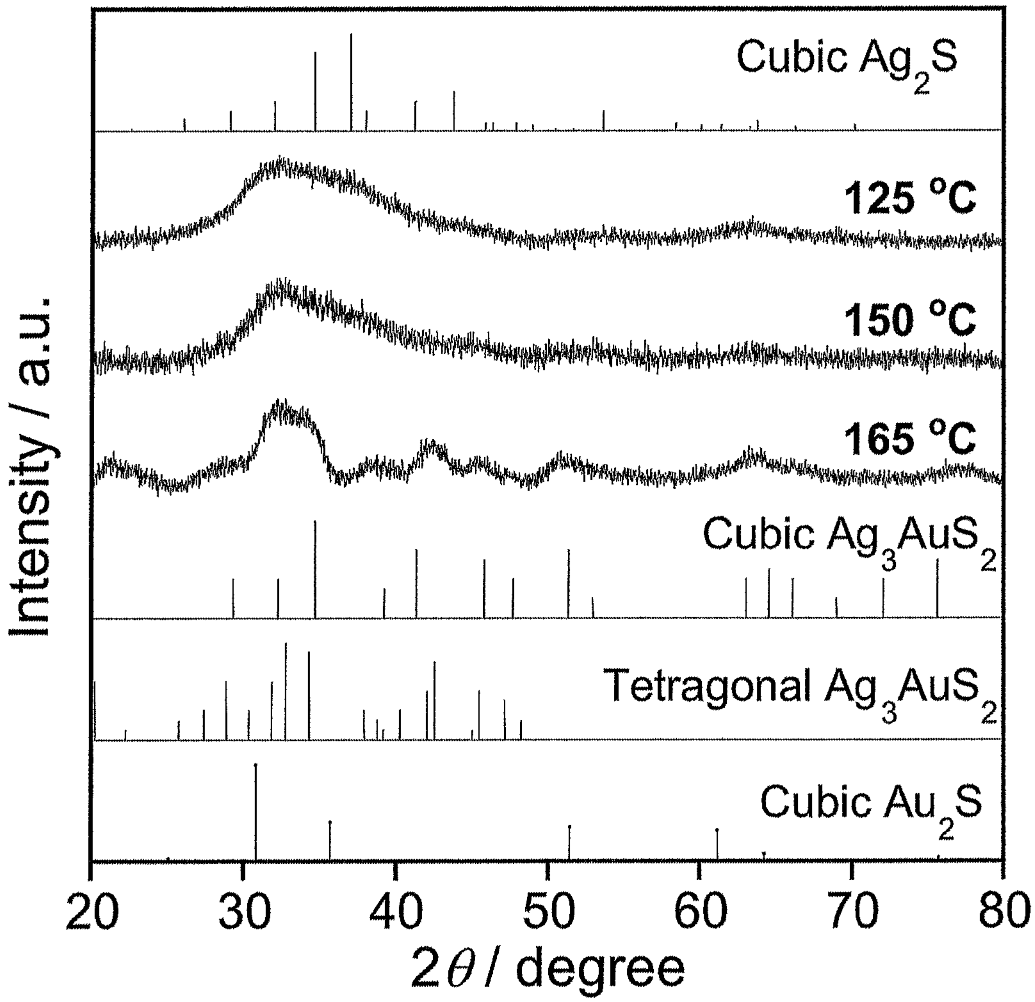
FIG. 17 is a view showing XRD diffraction patterns of the AgAuS semiconductor nanoparticles (reaction temperatures: 125° C., 150° C. and 165° C.) manufactured in Second Embodiment.

Furthermore, XRD analysis was performed on the semiconductor nanoparticles obtained at the reaction temperatures set to 125° C., 150° C. and 165° C. The analysis condition is the same as that in First Embodiment. FIG. 17 shows the diffraction pattern of each semiconductor nanoparticle. It was found from FIG. 17 that the semiconductor nanoparticle manufactured at 165° C. was more highly crystalline since each diffraction peak became sharp. When the diffraction patterns are considered together with the measurement results of the average particle diameters, it is suggested that the promotion of crystal growth by an increase in the reaction temperature increases the particle diameter of the semiconductor nanoparticle and enhances crystallinity. Based on what has been described above, it is considered that the semiconductor nanoparticle of the present invention can be manufactured at reaction temperatures of 100° C. to 175° C., but more preferable reaction temperatures are 165° C. or lower from the viewpoint of the emission quantum yield.

Industrial Applicability

As described above, the semiconductor nanoparticle of the present invention that is composed of a AgAuS-based compound and has a novel composition is capable of exhibiting favorable light characteristics. In addition, the AgAuS-based compound is a low-toxic biocompatible compound. The semiconductor nanoparticle of the present invention is expected to be applied to light-emitting elements and fluorescent substances that are used for display devices, marker substances for detecting bio-related substances and the like or photoelectric conversion elements or light-receiving elements, which are mounted in solar cells, light sensors and the like.

In addition, it is also possible to obtain a semiconductor nanoparticle capable of exhibiting emission and extinction characteristics in the near-infrared range based on the present invention. As photoelectric conversion elements for which responsiveness in the near-infrared range has been emphasized recently, there are light-receiving elements that are applied to LIDAR (light detection and ranging) or short-wave infrared (SWIR) image sensors. The semiconductor nanoparticle of the present invention is expected to be applied to such photoelectric conversion elements that operate in the near-infrared range.

What is claimed is:

1. A semiconductor nanoparticle comprising:

a semiconductor crystal of a compound containing Ag, Au and S as essential constitutional elements, wherein the compound has a total content of Ag, Au and S of 95 mass % or more, and is a AgAuS ternary compound represented by the general formula $Ag_{(nx)}Au_{(ny)}S_{(nz)}$, wherein n is any positive integer; x, y and z represent proportions of the number of atoms of the respective atoms of Ag, Au and S in the compound, and are real numbers satisfying $0<x, y, z\leq 1$; and $(x+y)/(2z)$ is 0.79 to 0.95.

2. The semiconductor nanoparticle according to claim 1, wherein x/y is 1/7 or more and 7 or less.

3. The semiconductor nanoparticle according to claim 2, wherein a value of $x/(x+y)$ is a real number of 0.33 or more and 0.78 or less.

4. The semiconductor nanoparticle according to claim 1, having an average particle diameter of 2 nm or more and 20 nm or less.

5. The semiconductor nanoparticle according to claim 1, having at least any of an alkylamine having 4 to 20 carbon atoms in an alkyl chain, an alkenylamine having 4 to 20 carbon atoms in an alkenyl chain, an alkylcarboxylic acid having 3 to 20 carbon atoms in an alkyl chain, an alkenylcarboxylic acid having 3 to 20 carbon atoms in an alkenyl chain, an alkanethiol having 4 to 20 carbon atoms in an alkyl chain, a trialkylphosphine having 4 to 20 carbon atoms in an alkyl chain, a trialkylphosphine oxide having 4 to 20 carbon atoms in an alkyl chain, triphenylphosphine and triphenylphosphine oxide as a protective agent bonded to a surface thereof.

6. The semiconductor nanoparticle according to claim 1, wherein a long wavelength-side absorption edge wavelength of an absorption spectrum is 600 nm or higher.

* * * * *